US010086024B2

(12) United States Patent
Kovarik

(10) Patent No.: US 10,086,024 B2
(45) Date of Patent: Oct. 2, 2018

(54) METHOD AND SYSTEM FOR PROTECTING HONEY BEES, BATS AND BUTTERFLIES FROM NEONICOTINOID PESTICIDES

(71) Applicant: Joseph E. Kovarik, Englewood, CO (US)

(72) Inventor: Joseph E. Kovarik, Englewood, CO (US)

( * ) Notice: Subject to any disclaimer, the term of this patent is extended or adjusted under 35 U.S.C. 154(b) by 0 days.

(21) Appl. No.: 15/379,579

(22) Filed: Dec. 15, 2016

(65) Prior Publication Data

US 2017/0151293 A1   Jun. 1, 2017

Related U.S. Application Data

(63) Continuation-in-part of application No. 15/270,034, filed on Sep. 20, 2016, now Pat. No. 9,750,802, which is a continuation of application No. 14/954,074, filed on Nov. 30, 2015, now Pat. No. 9,457,077.

(60) Provisional application No. 62/277,568, filed on Jan. 12, 2016, provisional application No. 62/277,571, filed on Jan. 12, 2016, provisional application No. 62/278,046, filed on Jan. 13, 2016.

(51) Int. Cl.
| | |
|---|---|
| *A61K 35/74* | (2015.01) |
| *A61K 35/741* | (2015.01) |
| *A61K 35/742* | (2015.01) |
| *A61K 35/745* | (2015.01) |
| *A61K 35/747* | (2015.01) |
| *A61K 35/748* | (2015.01) |
| *C12N 1/20* | (2006.01) |

(52) U.S. Cl.
CPC ............ *A61K 35/747* (2013.01); *A61K 35/74* (2013.01); *A61K 35/741* (2013.01); *A61K 35/742* (2013.01); *A61K 35/745* (2013.01); *A61K 35/748* (2013.01); *C12N 1/20* (2013.01)

(58) Field of Classification Search
None
See application file for complete search history.

(56) References Cited

U.S. PATENT DOCUMENTS

| | | | |
|---|---|---|---|
| 3,178,341 A | 4/1965 | Hamill et al. | |
| 4,687,841 A | 8/1987 | Spilburg et al. | |
| 4,720,486 A | 1/1988 | Spilburg et al. | |
| 6,287,610 B1 | 9/2001 | Bowling et al. | |
| 6,569,474 B2 | 5/2003 | Clayton et al. | |
| 7,267,975 B2 | 9/2007 | Strobel et al. | |
| 7,820,420 B2 | 10/2010 | Whitlock | |
| 7,846,711 B2 | 12/2010 | Boettner et al. | |
| 8,349,313 B2 | 1/2013 | Smith et al. | |
| 8,481,299 B2 | 7/2013 | Gueniche | |
| 8,496,914 B2 | 7/2013 | Bonfiglio | |
| 8,585,588 B2 | 11/2013 | Kovarik et al. | |
| 8,685,389 B2 | 4/2014 | Baur | |
| 8,701,671 B2 | 4/2014 | Kovarik | |
| 8,758,764 B2 | 6/2014 | Masignani et al. | |
| 8,815,538 B2 | 8/2014 | Lanzalaco et al. | |
| 8,951,775 B2 | 2/2015 | Castiel | |
| 9,011,834 B1 | 4/2015 | McKenzie et al. | |
| 9,028,841 B2 | 5/2015 | Henn et al. | |
| 9,131,884 B2 | 9/2015 | Holmes | |
| 9,234,204 B2 | 1/2016 | Qvit-Raz et al. | |
| 9,288,981 B2 | 3/2016 | Gandhi et al. | |
| 2002/0009436 A1 | 1/2002 | Doyle et al. | |
| 2003/0206995 A1 | 11/2003 | Bowling et al. | |
| 2007/0054008 A1 | 3/2007 | Clayton et al. | |
| 2007/0207955 A1 | 9/2007 | Tanihara et al. | |
| 2009/0205083 A1 | 8/2009 | Gupta et al. | |
| 2010/0029832 A1 | 2/2010 | Pinnavaia et al. | |
| 2012/0027786 A1 | 2/2012 | Gupta | |
| 2012/0142548 A1 | 6/2012 | Corsi et al. | |
| 2012/0276143 A1 | 11/2012 | O'Mahony et al. | |
| 2012/0276525 A1 | 11/2012 | Kovarik et al. | |
| 2013/0064796 A1 | 3/2013 | Hamdi | |
| 2013/0157876 A1 | 6/2013 | Lynch et al. | |
| 2013/0259834 A1 | 10/2013 | Klaenhammer et al. | |
| 2013/0315869 A1 | 11/2013 | Qimron et al. | |
| 2014/0044677 A1 | 2/2014 | Qvit-Raz et al. | |
| 2014/0045744 A1 | 2/2014 | Gordon | |
| 2014/0065209 A1 | 3/2014 | Putaala et al. | |
| 2014/0065218 A1 | 3/2014 | Lang et al. | |
| 2014/0068797 A1 | 3/2014 | Doudna et al. | |
| 2014/0154290 A1 | 6/2014 | Peters et al. | |
| 2014/0212520 A1 | 7/2014 | Del Vecchio et al. | |
| 2014/0255351 A1 | 9/2014 | Berstad et al. | |
| 2014/0349405 A1 | 11/2014 | Sontheimer et al. | |
| 2014/0363441 A1 | 12/2014 | Grandea, III et al. | |
| 2014/0377278 A1 | 12/2014 | Elinav et al. | |
| 2015/0017227 A1 | 1/2015 | Kim | |
| 2015/0064138 A1 | 3/2015 | Lu et al. | |
| 2015/0071957 A1 | 3/2015 | Kelly | |

(Continued)

FOREIGN PATENT DOCUMENTS

CN          103937722 A   *  7/2014

OTHER PUBLICATIONS

Wang et al. ACS Synth. Biol. Apr. 2016, 5, 721-732.*

(Continued)

*Primary Examiner* — Oluwatosin A Ogunbiyi

(74) *Attorney, Agent, or Firm* — Sheridan Ross P.C.

(57) ABSTRACT

A method and system for the treatment of honey bees (*Apis mellifera*), bats, and butterflies protects them from various life threatening conditions, including Colony Collapse Disorder, white nose syndrome, etc. and in particular, provides honey bees, bats and butterflies with the ability to assimilate and degrade neonicotinoids.

8 Claims, 3 Drawing Sheets

(56) References Cited

U.S. PATENT DOCUMENTS

Figure 1:
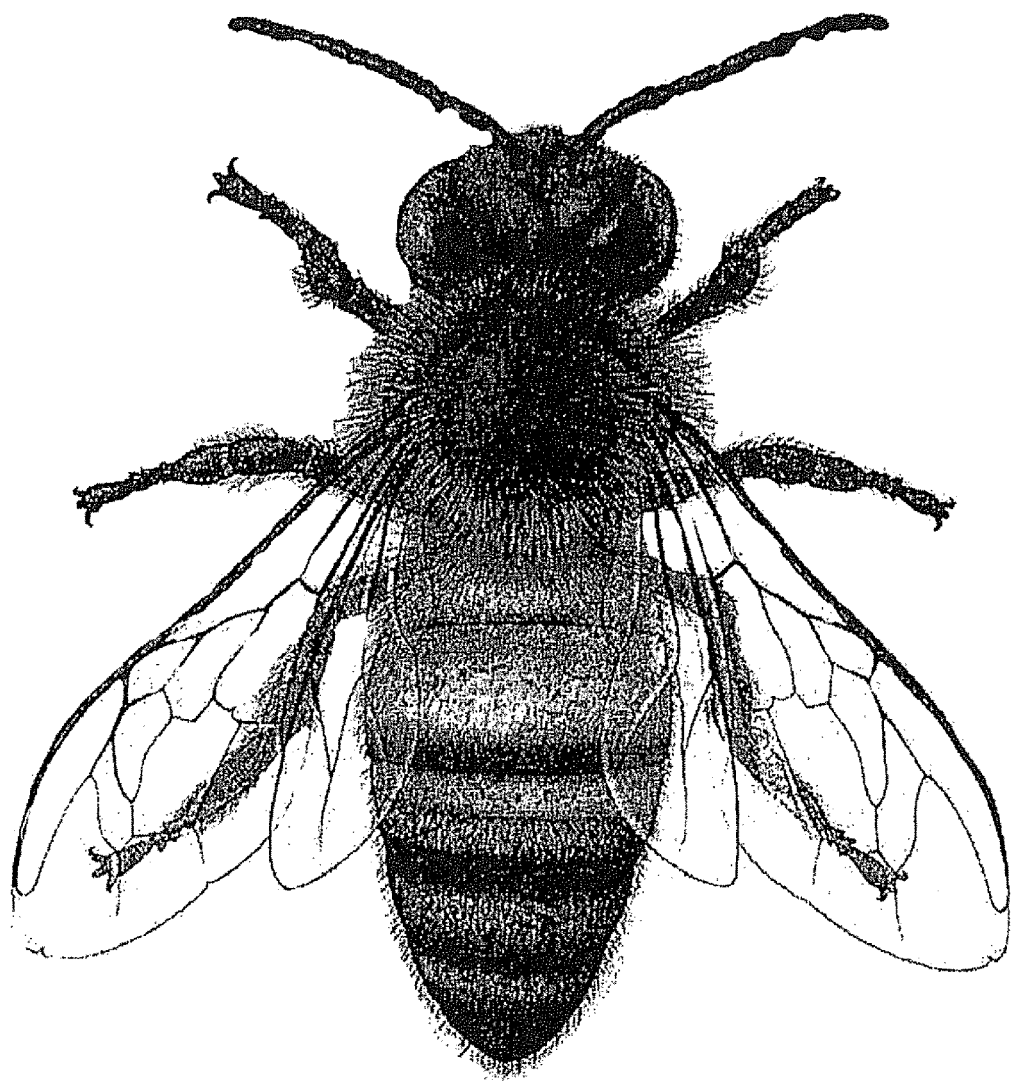
Figure 2:
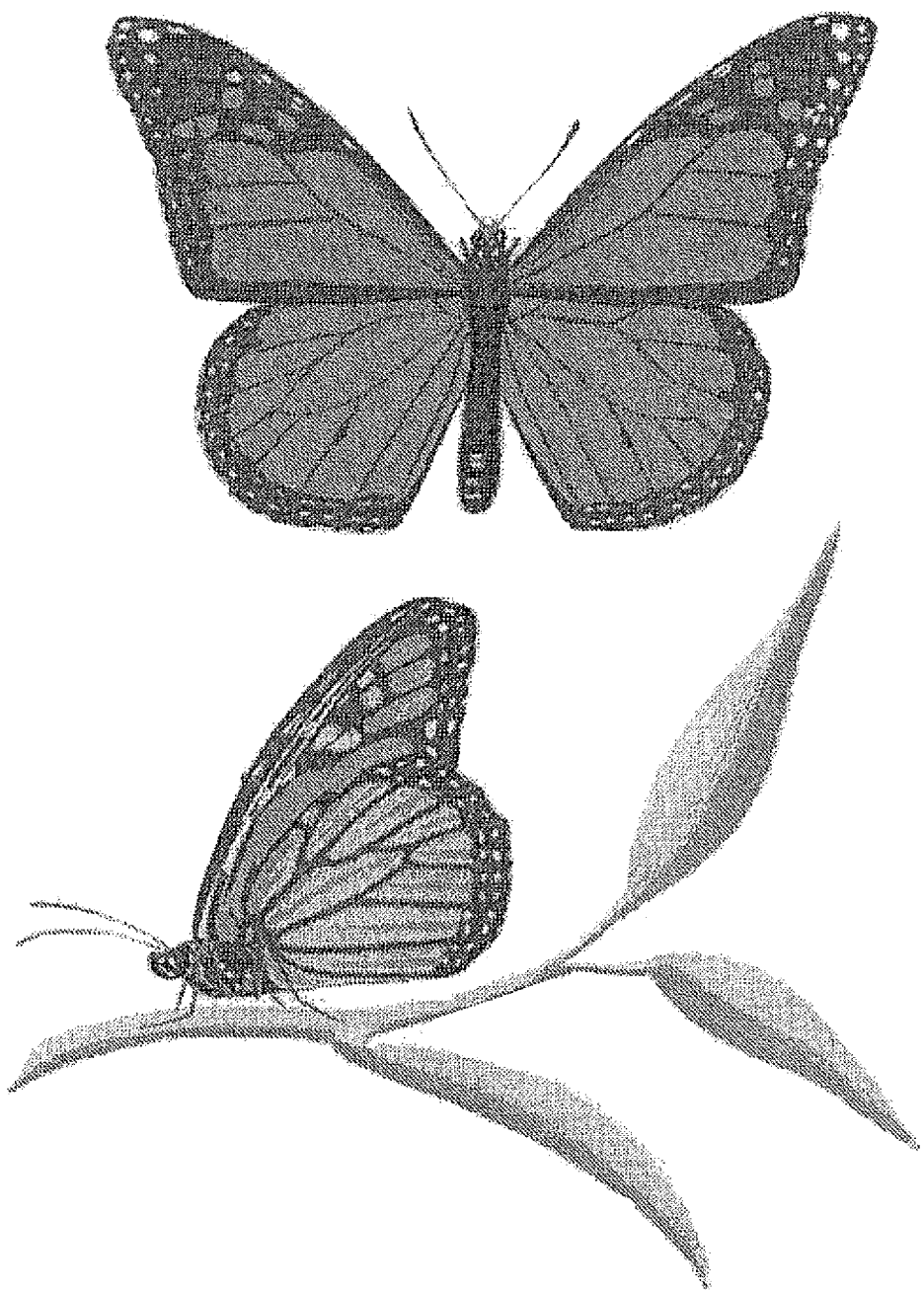
Figure 3:
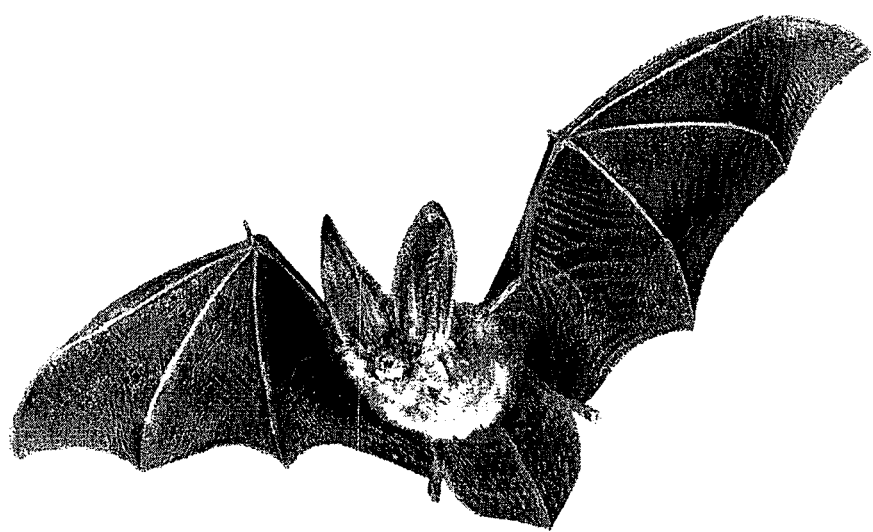

| | | |
|---|---|---|
| 2015/0086581 A1 | 3/2015 | Li et al. |
| 2015/0093473 A1 | 4/2015 | Barrangou |
| 2015/0132263 A1 | 5/2015 | Liu et al. |
| 2015/0166641 A1 | 6/2015 | Goodman |
| 2015/0190435 A1 | 7/2015 | Henn et al. |
| 2015/0216917 A1 | 8/2015 | Jones |
| 2015/0353901 A1 | 12/2015 | Liu |
| 2015/0361436 A1 | 12/2015 | Hitchcock |
| 2015/0374607 A1 | 12/2015 | Lanzalaco et al. |
| 2016/0008412 A1 | 1/2016 | Putaala et al. |
| 2016/0040216 A1 | 2/2016 | Wilder |
| 2016/0089315 A1 | 3/2016 | Kleinberg et al. |
| 2016/0151427 A1 | 6/2016 | Whitlock et al. |
| 2016/0168594 A1 | 6/2016 | Zhang et al. |
| 2016/0206668 A1 | 7/2016 | Kort et al. |
| 2016/0271106 A1 | 9/2016 | Shi et al. |
| 2016/0271189 A1 | 9/2016 | Cutcliffe |
| 2016/0314281 A1 | 10/2016 | Apte |
| 2016/0354416 A1 | 12/2016 | Gajewski et al. |
| 2017/0020932 A1 | 1/2017 | Cutcliffe et al. |
| 2017/0021011 A1 | 1/2017 | Kovarik et al. |
| 2017/0071986 A1 | 3/2017 | Kovarik et al. |

OTHER PUBLICATIONS

Team British Columbia, Probeeotics UBC Igem 2015, pp. 1-46.
Team British Columbia, Welcome to the UBC Igem Wiki. pp. 1-4, http://2015.igem.org/Team: British_Columbia.

* cited by examiner

METHOD AND SYSTEM FOR PROTECTING HONEY BEES, BATS AND BUTTERFLIES FROM NEONICOTINOID PESTICIDES

RELATED APPLICATIONS

This application claims priority from U.S. Provisional Patent Application Ser. No. 62/277,568, filed on Jan. 12, 2016, from U.S. Provisional Patent Application Ser. No. 62/277,571, filed on Jan. 12, 2016 and U.S. Provisional Patent Application Ser. No. 62/278,046, filed on Jan. 13, 2016.

This application also is a continuation-in-part of U.S. patent application Ser. No. 15/270,034, filed on Sep. 20, 2016, which is a continuation-in-part of U.S. patent application Ser. No. 14/954,074, filed on Nov. 30, 2015 (now U.S. Pat. No. 9,457,077, issued Oct. 4, 2016).

The entire disclosure of the prior applications are considered to be part of the disclosure of the accompanying application and are hereby incorporated by reference.

FIELD OF THE INVENTION

The present invention relates to a method and system for the treatment of honey bees (*Apis mellifera*), bats, and butterflies to protect them from various life threatening conditions, including Colony Collapse Disorder, white nose syndrome, etc. and in particular, is directed to providing honey bees, bats and butterflies with the ability to assimilate and degrade neonicotinoids.

BACKGROUND OF THE INVENTION

Pollinating insects are key to the evolutionary and ecological success of flowering plants and enable much of the diversity in the human diet. Bees are arguably one of the most important beneficial insects worldwide. Their positive impact can be measured by the value they contribute to the agricultural economy, their ecological role in providing pollination services, and the hive products they produce. The honey bee is credited with approximately 85% of the pollinating activity necessary to supply about one-quarter to one-third of the nation's food supply. Over 50 major crops in the United States either depend on honey bees for pollination or produce more abundantly when honey bees are plentiful.

Approximately 90% of flowering plants—corresponding to nearly three quarters of global agricultural crops—use pollinators to set seed and fruit. Populations of several species of pollinators, however, are in decline throughout the world, threatening the stability of our ecosystems and productivity of our agricultural landscapes.

Bees are vital to global biodiversity and food security through their pollination of plants, including several key crops. Honey bees, however, are exposed to myriad of stressors including pests, pathogens, pesticides, poor nutrition due to monocropping and habitat loss leading to extreme colony losses.

In about 2006-2007, the discovery of the devastating effects of Colony Collapse Disorder on US honey bee populations was first noticed. Overwhelming evidence now suggests that numerous wild and managed bee populations are in decline. This has led to concerns over human food security and maintenance of biodiversity. Recent losses of honeybee colonies have been linked to several non-exclusive factors; such as pests, parasites, pesticides (e.g., neonicotinoids) and other toxins. In the last 20 years, the bee-keeping sector registered very consistent losses worldwide, in terms of bee numbers and productivity. Queen health is crucial to colony survival of social bees. Recently, queen failure has been proposed to be a major driver of managed honey bee colony losses. The role of queens (primary reproductive females that can produce diploid offspring) in social bee colony survival is indispensable. There have been anecdotal reports of 'poor quality queens' (i.e. queen failure) of the western honey bee (*Apis mellifera*; hereafter honey bee), throughout the northern hemisphere.

Common microbial pathogens appear to be major threats to honey bees, while sublethal doses of pesticide may enhance their deleterious effects on honey bee larvae and adults. Honey bees are suffering from elevated colony losses in the northern hemisphere possibly because of a variety of emergent microbial pathogens, with which pesticides may interact to exacerbate their impacts.

More than six decades after the onset of wide-scale commercial use of synthetic pesticides and more than fifty years after Rachel Carson's Silent Spring, pesticides, particularly insecticides, arguably remain the most influential pest management tool around the globe. Nevertheless, pesticide use is still a controversial issue and is at the regulatory forefront in most countries. Neonicotinoids are suspected to pose an unacceptable risk to bees, partly because of their systemic uptake in plants. The European Union has therefore introduced a moratorium on three neonicotinoids as seed coatings in flowering crops that attract bees. The neonicotinoid class of chemical pesticides has recently received considerable attention because of potential risks it poses to ecosystem functioning and services. Ubiquitously used for management of harmful insects in the last decade, these systemic chemicals persist in the environment, thereby promoting their contact with non-target organisms such as pollinating bees.

Sub-lethal doses of neonicotinoids have been shown to negatively impact the health of honeybees. Understanding the effects of neonicotinoid insecticides on bees is vital because of reported declines in bee diversity and distribution and the crucial role bees have as pollinators in ecosystems and agriculture. Pollinators perform sophisticated behaviors' while foraging that require them to learn and remember floral traits associated with food. Neonicotinoid pesticides, at levels shown to occur in the wild, interfere with the learning circuits in the bee's brain. Pesticides have a direct impact on pollinator brain physiology. Disruption in this important function has profound implications for honeybee colony survival, because bees that cannot learn will not be able to find food. Both honey bees and bumble bees prefer sugar solutions laced with the neonicotinoids imidacloprid, clothianidin, and thiamethoxam over pure sugar water, presumably due to the nicotine-like addition that is so common in humans.

On Apr. 2, 2015, the EPA announced that it will not be approving new outdoor uses of neonicotinoids until pollinator risk assessments are complete. Tests include acute and chronic toxicity tests for adults and larvae, field feeding studies, foliage toxicity, residues in pollen and nectar, and realistic field experiments that look at long term effects.

Canola is becoming a favored crop in the prairies, with over a million acres (1700 square miles) to be planted in North Dakota alone this year. Bayer CropScience grows hybrid canola seed in Canada, and in an ironic twist, is thereby the largest renter of honey bee pollination services in Canada, and is thus highly motivated to ensure that the product does not harm bees. Virtually all canola seed is treated with clothianidin or its precursor, thiamethoxam.

There is therefore a long felt but unsolved need for a system and method to protect honey bees from the increasing use of neonicotinoid insecticides which are believed to be at least partially responsible for the recent demise of honey bee populations.

The corpses of hibernating bats were first found blanketing caves in the northeastern United States in 2006. The disease that killed them, caused by a cold-loving fungus called *Geomyces destructans*—and dubbed White-nose Syndrome (WNS) for the tell-tale white fuzz it leaves on bats' ears and noses—has since destroyed at least one million Bats, becoming one of the most precipitous wildlife decline in the past century in North America. WNS is a fungal disease that has its greatest impacts during bat hibernation and emergence. Bats in torpor experience reduced immune function, thus potentially compromising their ability to combat WNS. Fat reserves are metabolized during hibernation, a process that can mobilize contaminants to the brain and other tissues coincident with reduced immune function. CECs, such as PBDEs, bisphenol A, and triclosan, may further diminish immune competence.

Bats are especially vulnerable to chemical pollution. They're small—the little brown bat weighs just 8 grams—and can live for up to three decades. For their body size, bats live longer than any other order of mammal. Bats may be more susceptible than other mammals to the effects of low doses of bioaccumulative contaminants due to their annual life cycles, requiring significant fat deposition followed by extreme fat depletion during hibernation or migration, at which time contaminants may be mobilized into the brain and other tissues.

There is a growing body of science directly implicating neonicotinoid (neonic) pesticides in the significant decline of bees and other pollinators, including bats. Pollinator decline has been found on every continent in the world, and hundreds of pollinator species are on the verge of extinction. Since 2006, bees in the U.S. have been dying off or seemingly abandoning their hives—a phenomenon known as Colony Collapse Disorder. While there are many contributors to pollinator decline, two of the most important are the loss of habitat and the introduction and expansion of use of new pesticides on agricultural cropland. A specific concern centers on neonicotinoids, a relatively new class of systemic insecticides, often applied as a seed coating in commodity agriculture.

Neonicotinoids came into wide use in the early 2000s. Unlike older pesticides that evaporate or disperse shortly after application, neonicotinoids are systemic poisons. Applied to the soil or doused on seeds, neonicotinoid insecticides incorporate themselves into plant tissues, turning the plant itself into a tiny poison factory emitting toxin from its roots, leaves, stems, pollen, and nectar. As the name suggest, neonicotinoids are similar in structure to nicotine and paralyze or disorient insects by blocking a pathway that transmits nerve impulses in the insect's central nervous system.

Neonicotinoids are used to control a wide variety of insects. The first neonicotinoid, imidacloprid (Admire), became available in the United States in 1994 and is currently present in over 400 products on the market. Other neonic insecticides include acetamiprid, clothianidin, dinotefuran, nitenpyram, thiacloprid, and thiamethoxam. In 2006, neonicotinoids accounted for over 17 percent of the global insecticide market. Two of them—clothianidin and thiamethoxam—dominate the global market for insecticidal seed treatments and are used to coat the seeds of most of the annual crops planted around the world. In fact, more than 94 percent of the corn and more than 30 percent of the soy planted in the United States is pretreated with neonicotinoids.

The introduction of neonicotinoids into the agricultural marketplace occurred around the same time as the introduction of GMO crops in the mid-to-late 1990s. Monsanto and Syngenta, the undisputed leaders in patented genetically engineered seeds, also have close relationships with the leading global neonic producer, Bayer. Most new commodity crops are increasingly coming to farmers with stacked traits, which means more than one transgenic alteration. These genetically engineered and transplanted traits are marketed to farmers as providing benefits such as resistance to multiple herbicides, pests, funguses, heat and drought.

Seed treatment applications are prophylactic, meaning they are used whether or not there is any evidence of pest pressures. At least 30 percent of soybean seeds planted annually (approximately 22.5 million out of 75 million acres) are pretreated with neonic insecticides (two of the primary four being imidacloprid and thiamethoxam). But corn has the highest use and acreage with around 94 percent of U.S. corn treated with a neonicotinoid. That widespread use has quickly elevated the Midwest to the highest levels of neonicotinoid use in the country. These neonicotinoids don't stay in the plants and soil however, but find their ways into the water as well. A recent U.S. Geological Survey report confirmed that neonicotinoids were common in streams throughout the Midwest. Bats frequently forage in aquatic and terrestrial habitats that may be subjected to discharges from wastewater treatment plants, agricultural operations, and other point and nonpoint sources of contaminants.

Death is not the only outcome of pesticide exposure. Sub-lethal doses of neonicotinoids can disrupt pollinators' cognitive abilities, communication and physiology. Neonicotinoids also have harmful synergistic impacts on pollinators in combination with other chemicals in the field, compounding their effects. Scientists have shown in multiple studies that the combined presence of neonicotinoids and some fungicides can increase the potency of neonicotinoids by more than 1,000-fold. In addition to their toxicity, neonicotinoids persist in plants much longer than most other insecticides, thereby compounding their impact on pollinators. They can reside in plant tissues for over a year, and some can persist for even longer in the soil. This means pollinators and other animals are exposed to the chemicals for extended periods of time and in some regions year-round.

There is a desperate need for an effective treatment to advert the destruction of bat species that has been observed over the last decade. The ramifications of the elimination of such an important pollinator, such as the bat, will have tremendous and as yet unforeseen negative effects on the environment. A need for a treatment is therefore long felt and unsolved. The present invention is directed to a method and system that achieves this objective.

The annual migration of North America's monarch butterfly (*Danaus plexippus* Kluk (Lepidoptera: Nymphalidae) is a unique and amazing phenomenon. The monarch is the only butterfly known to make a two-way migration as birds do. Unlike other butterflies that can overwinter as larvae, pupae, or even as adults in some species, monarchs cannot survive the cold winters of northern climates. Using environmental cues, the monarchs know when it is time to travel south for the winter. Monarchs use a combination of air currents and thermals to travel long distances. Some fly as far as 3,000 miles to reach their winter home. The multi-generational migration of North American monarch butterflies between breeding grounds in the northern U.S. and southern Canada and wintering grounds in central Mexico and coastal California is one of the world's most spectacular natural events. The interest in monarchs and their fascinating, visible biology is demonstrated by monarch butterflies being the official insect or butterfly of seven U.S. states; celebrated via festivals in Mexico, the United States, and Canada; the focus of science curricula; and the subject of multiple citizen-science projects.

Monarch butterfly populations have declined precipitously in North America in the last twenty years. This decline has commonly been linked to loss of milkweeds (*Asclepias* species) from farmer's fields. Monarch caterpillars are dependent on milkweeds. The ability of farmers to kill them with the Monsanto herbicide Roundup (glyphosate) has therefore led to this herbicide being considered as a major contributor to the decline of the monarch butterfly. Adult monarch butterflies feed on nectar that provides sugars and other nutrients. Monarch butterflies migrate to Mexican forests for overwintering. Overwintering monarchs reduce their metabolism and limit their feeding.

The introduction of neonicotinoids into the agricultural marketplace occurred around the same time as the introduction of GMO crops in the mid-to-late 1990s. Monsanto and Syngenta, the undisputed leaders in patented genetically engineered seeds, also have close relationships with the leading global neonic producer, Bayer. Most new commodity crops are increasingly coming to farmers with stacked traits, which means more than one transgenic alteration. These genetically engineered and transplanted traits are marketed to farmers as providing benefits such as resistance to multiple herbicides, pests, funguses, heat and drought.

Seed treatment applications are prophylactic, meaning they are used whether or not there is any evidence of pest pressures. At least 30 percent of soybean seeds planted annually (approximately 22.5 million out of 75 million acres) are pretreated with neonic insecticides (two of the primary four being imidacloprid and thiamethoxam). But corn has the highest use and acreage with around 94 percent of U.S. corn treated with a neonicotinoid. That widespread use has quickly elevated the Midwest to the highest levels of neonicotinoid use in the country. These neonicotinoids don't stay in the plants and soil however, but find their ways into the water as well. A recent U.S. Geological Survey report confirmed that neonicotinoids were common in streams throughout the Midwest.

In 1999, common milkweed, the monarch's food plant, was found in half of corn and soybean fields, but in only 8% of them a decade later. Glyphosatetolerant GM crops are grown in the same fields each year. Once absorbed, glyphosate is translocated to the roots and therefore the milkweed does not regenerate. It has been shown that clothianidin, a very long-acting systemic neonicotinoid insecticide, has contributed to the decline of monarch butterflies. USDA researchers have identified the neonicotinoid insecticide clothianidin as a likely contributor to monarch butterfly declines in North America. Neonicotinoids have been strongly implicated in pollinator declines worldwide. As shown by a report from a task force of the International Union of Nature Conservation based in Switzerland, neonicotinoids, such as clothianidin (Bayer), are a particular hazard because, unlike most pesticides, they are soluble molecules. From soil or seed treatments they can reach nectar and are found in pollen.

USDA researchers have shown that clothianidin can have effects on monarch caterpillars at doses as low as 1 part per billion. The effects seen in experiments were on caterpillar size, caterpillar weight, and caterpillar survival. The lethal dose (LC50) they found to be 15 parts per billion. The caterpillars in their experiments were exposed to clothianidin-treated food for only 36 hrs, however. The researchers therefore noted that in agricultural environments caterpillar exposure would likely be greater than in their experiments. Furthermore, that butterfly caterpillars would be exposed in nature to other pesticides, including other neonicotinoids. In sampling experiments from agricultural areas in South Dakota the researchers found that milkweeds had on average over 1 ppb clothianidin. On this basis the USDA researchers concluded that "neonicotinoids could negatively affect larval monarch populations."

Neonicotinoids are now the most widely used pesticides in the world. Neonicotinoids are neurotoxins that are partially banned in the EU. There has been negligible research on the effects of neonicotinoids on butterflies. There is a desperate need for an effective treatment to advert the destruction of monarch butterflies that has been observed over the last decade. The ramifications of the elimination of the monarch butterfly will have tremendous and as yet unforeseen negative effects on the environment. A need for a treatment is therefore long felt and unsolved. The present invention is directed to a method and system that achieves this objective.

SUMMARY OF THE INVENTION

Certain aspects of the present invention are directed to employing genes from the microbe *ochrobactrum intermedium* such that honey bees are able to assimilate and degrade neonicotinoids. Other embodiments employ innoculaton of honey bees with a culture of neonicotinoid degrading bacteria, such as one or more of *ochrobactrum intermedium, Agrobacterium tumefaciens* S33, *Apergillus oryzae, Pseudomonas putida* S16*; Arthrobacter nicotinovarans, microsporum gypseum, pellicularia filamentosa* JTS-208, *pseudomonas* sp. 41; *Microsporum gypseum; Pseudomonas* ZUTSKD; *aspergillus oryzae* 112822; and *ochrobactrum intermedium* DN2. Preferably wherein the bacteria collection or culture comprises *ochrobactrum intermedium*, collection number CGMCC NO. 8839. The invention further provides applications of the *ochrobactrum intermedium* to foster degradation of neonicotinoid insecticides by the honey bee while the microbe exists in the gut of the honey bee.

Honey bees host a multitude of species of microbes that positively impact bee health. The guts of honey bee workers contain a distinctive community of bacterial species. They are microaerophilic or anaerobic. These species include both Gram negative groups, such as *Gilliamella apicola* and *Snodgrassella alvi*, and Gram positive groups such as certain *Lactobacillus* and *Bifidobacterium* species. These gut bacterial species appear to have undergone long term coevolution with honey bee and, in some cases, bumble bee hosts. Prediction of gene functions from genome sequences suggests roles in nutrition, digestion, and potentially in defense against pathogens. In particular, genes for sugar utilization and carbohydrate breakdown are enriched in *G. apicola* and the *Lactobacillus* species.

CRISPR (Clustered Regularly Interspaced Short Palindromic Repeats) is a prokaryotic adaptive defense system that provides resistance against alien replicons such as viruses and plasmids. CRISPRs evolved in bacteria as an adaptive immune system to defend against viral attack. Upon exposure to a virus, short segments of viral DNA are integrated into the CRISPR locus. RNA is transcribed from a portion of the CRISPR locus that includes the viral sequence. That RNA, which contains sequence complimentary to the viral genome, mediates targeting of a Cas9 protein to a target sequence in the viral genome. The Cas9 protein cleaves and thereby silences the viral target. In preferred embodiments, rather than using CRISPR-Cas, one employs the CRISPR-associated endonuclease Cpf1. e.g. a CRISPR from *Prevotella* and *Francisella* 1 (Cpf1) nuclease for CRISPR-based genome editing (and incorporating 20150252358 to Maeder by this reference).

CRISPR has a certain protein in it called Cas9 that acts like a scissor as it recognizes specific sequences of DNA and cuts it enabling one to perform genome-editing of a bacterial genome in a person's microbiome. There exists another CRISPR system, CRISPR-Cpf1 that is even more preferred for use in microbial systems. Cpf1 is important in bacterial immunity and is well adapted to slice target DNAs. Cpf1 prefers a "TTN" PAM motif that is located 5' to its protospacer target—not 3', as per Cas9, making it distinct in having a PAM that is not G-rich and is on the opposite side of the protospacer. Cpf1 binds a crRNA that carries the protospacer sequence for base-pairing the target. Unlike Cas9, Cpf1 does not require a separate tracrRNA and is devoid of a tracrRNA gene at the Cpf1-CRISPR locus, which means that Cpf1 merely requires a cRNA that is about 43 bases long—of which 24 nt is protospacer and 19 nt is the constitutive direct repeat sequence. In contrast, the single RNA that Cas9 needs is still about. 100 nt long. Cpf1 is apparently directly responsible for cleaving the 43-base cRNAs apart from the primary transcript.

With respect to the cleavage sites on the target DNA, the cut sites are staggered by about 5 bases, thus creating "sticky overhangs" to facilitate gene editing via NHEJ-mediated-ligation of DNA fragments with matching ends. The cut sites are in the 3' end of the protospacer, distal to the 5' end where the PAM is. The cut positions usually follow the 18th base on the protospacer strand and the 23rd base on the complementary strand (the one that pairs to the crRNA). In Cpf1 there is a "seed" region close to the PAM in which single base substitutions completely prevent cleavage activity. Unlike the Cas9 CRISPR target, the cleavage sites and the seed region do not overlap. One advantage of the present invention, as compared to techniques that rely on CRISPR systems to modify mammalian cells, is that the system and method of preferred embodiments are directed to bacterial systems—rather than eukaryotic systems. It is believed that Cpf1 may be better than Cas9 for mediating insertions of DNA, namely because its guide RNA is only 43 bases long, making it feasible to purchase directly synthesized guide RNAs for Cpf1, with or without chemical modifications to enhance stability.

CRISPR systems may be employed to insert desired genes into the above mentioned (as well as others) microbes that inhabit the honey bee gut so as to degrade particular insecticides, including neonicotinoids. The bee microbiome enhances host functions, contributing to host health and fitness. One aspect of the present invention is directed to improving honey bee fitness by modifying the honey bee microbiome, thus engineering evolved microbiomes with specific effects on the host honey bee fitness. Thus, by employing host-mediated microbiome selection, one is able to select and modify microbial communities indirectly through the host, thus influencing the honey bee microbiome and positively affecting honey bee fitness. The methods that may be used to impose artificial selection on the honey bee microbiome include various techniques known to those of skill in the art, including CRISPR-Cas and Cpf1 systems.

Thus, while particular cultures of particular microbes can be purposefully included into bee populations so as to inhabit their gut microbiome, and by doing so, providing the honey bees with the ability to degrade neonicotinoids, other embodiments are directed to engineering a modification of the honey bee gut microbes that do not already possess such neonicotinoid degradation genes.

Detoxification gene inventory reduction may reflect an evolutionary history of consuming relatively chemically benign nectar and pollen. Relative to most other insect genomes, the western honey bee *Apis mellifera* has a deficit of detoxification genes. Thus, certain embodiments are directed to the development of predictable microbiome-based biocontrol strategies by providing the ability of insects such as the honey bee, to degrade or otherwise assimilate insecticides or other chemical agents, including neonicotinoids. Such a novel biocontrol strategy can not only be used to suppress pathogens, but can also be effectively used to establish microbiomes in a desirable beneficial composition for particular purposes.

In certain embodiments, xenobiotic detoxification is employed to address the problems associated with the honey bee Colony Collapse Disorder. In particular embodiments, the conversion of lipid-soluble substances to water-soluble, excretable metabolites is achieved. In a primary detoxification step, a toxin structure is enzymatically altered and rendered unable to interact with lipophilic target sites. Such functionalization is effected primarily by cytochrome P450 monooxygenases (P450) and carboxylesterases (CCE), although other enzymes, including flavin-dependent monooxygenases and cyclooxygenases may also be employed. Further reactions typically involve conjugation of products of the above referenced step to achieve detoxification for solubilization and transport. Glutathione-S-transferases (GST) are the principal enzymes used, although other enzymes in insects may include glycosyltransferases, phosphotransferases, sulfotransferases, am inotransferases, and glycosidases. Nucleophilic compounds can be rendered hydrophilic by UDP-glycosyltransferases. The final stage of detoxification involves transport of conjugates out of cells for excretion. Among the proteins involved in this process are multidrug resistance proteins and other ATP-binding cassette transporters.

In the gut of the honey bee, a distinctive microbial community has been identified that is composed of a taxonomically restricted set of species specific to social bees. Despite the ecological and economical importance of honey bees and the increasing concern about population declines, the role of their gut symbionts for colony health and nutrition is largely unknown.

Long-term antibiotic treatment has caused the bee gut microbiota to accumulate resistance genes, drawn from a widespread pool of highly mobile loci characterized from pathogens and agricultural sites. 50 years of using antibiotics in beekeeping in the United States has resulted in extensive tetracycline resistance in the gut microbiota. Since the 1950s, the antibiotic oxytetracycline has been widely applied to colonies of bees in the United States to control larval foulbrood diseases caused by the bacteria *Melissococcus pluton* and *Paenibacillus larvae*; oxytetracycline was the only antibiotic approved for use in beekeeping until 2005.

When antibiotics are used for controlling infections by pathogens, they also impact other microbes, including the beneficial bacteria present in healthy hosts. The selective force imposed by an antibiotic can cause the accumulation of resistance determinants, which are often encoded on mobile genetic elements that are readily transferred among community members. The impact of antibiotics on the gut microbiota of honey bees is a particular concern, since gut communities may act as reservoirs for resistance genes that can be transferred to pathogens and also since perturbation of gut microbiota by antibiotic treatments could disrupt functions beneficial to the honey bee, butterflies and bats. Thus, in certain aspects of the present invention, restoring antibiotic resistance is one objective and this can be achieved via CRISPR-Cas modifications.

Compared to the gut microbiota of humans and other mammals, the honeybee gut microbiota provides a distinctive and relatively simple bacterial community. The honeybee has eight characteristic bacterial species that together comprise over 95% of the gut bacteria in adult worker bees. The eight bacterial species known to dominate the honeybee gut microbiota, primarily the Gram-negative members of this community are referred to via previous designations: "Alpha1" and "Alpha2" from the Alphaproteobacteria, *Snodgrassella alvi* from the Betaproteobacteria, *Gilliamella apicola* and "Gamma2" from the Gammaproteobacteria, "Firm4" and "Firm5" from the Firmicutes, and "Bifido" from the Bifidobacteriaceae. Any one or more of these bacteria can be modified to express particular genes that have been shown (for example by its inclusion in the bacteria *ochrobactrum intermedium*, to degrade neonicotinoids in a manner that preserves honey bee health.

Another aspect of the present invention is directed to addressing how we can stem the tide of bat decline by modifying the gut microbiota of bats so as to enable the bats to degrade various materials, including neonicotinoids, thus providing a method and system to assist in the survival and reproduction of bats. Both skin and gut microbiomes are involved in certain embodiments of the present invention. In certain embodiments, a treatment to prevent or at least reduce the occurrence and ramifications from White-nose syndrome, caused by the fungal skin pathogen *Pseudogymnoascus destructans*, is set forth, such treatment holding promise to avert the threat that several hibernating bat species may go extinct and offering one of the only effective treatment strategies for such condition. The skin microbiome of the bat is believed to play an important role in an effective treatment for WNS. In certain embodiments, bacteria of the genus *Pseudomonas* are employed to adversely affect the growth of the *P. destructans*. While in certain embodiments, bacteria found naturally occurring on bats are employed to inhibit the growth of *P. destructans*, in other embodiments, modified bacteria, preferably via the use of a CRISPR-Cas or Cpf1 system, is employed to enhance the growth of particular bacteria on the skin of bats, so as to counter the effects of WNS, notably by inhibiting the growth of *P. destructans*. These modified bacteria are thus employed as a skin probiotic to protect bats from white-nose syndrome.

Yet another aspect of the present invention is directed to addressing how to stem the tide of butterfly decline, and in particular Monarch butterfly declines, by modifying the gut microbiota of monarch butterflies so as to enable the butterflies to degrade neonicotinoids, thus providing a method and system to assist in the survival and reproduction of the monarch butterfly. Herein after, while emphasis is placed on Monarch butterflies, one of skill in the art will appreciate the application of the present invention to other pollinators, such as other butterflies, moths, etc. Monarch butterflies frequently consume milkweed in and near agroecosystems and consequently may be exposed to pesticides like neonicotinoids. One aspect of the present invention is directed to addressing how to stem the tide of monarch butterfly decline by modifying the gut microbiota of monarch butterflies so as to enable the butterflies to degrade neonicotinoids, thus providing a method and system to assist in the survival and reproduction of the monarch butterfly.

One will appreciate that this Summary of the Invention is not intended to be all encompassing one of skill in the art will appreciate that the entire disclosure, as well as the incorporated references, provides a basis for the scope of the present invention as it may be claimed now and in future applications.

BRIEF DESCRIPTION OF THE FIGURES

FIG. 1 is a depiction of a honeybee, one of the major pollinators that is assisted by employing the method and system of the present invention.

FIG. 2 is a depiction of a Monarch butterfly, which is also a pollinator that is assisted by employing the method and system of the present invention.

FIG. 3 is a depiction of a bat, which is yet another pollinator that is assisted by employing the method and system of the present invention.

DETAILED DESCRIPTION OF PREFERRED EMBODIMENTS OF THE PRESENT INVENTION

Impacts to honey bees from sublethal exposure to imidacloprid in the presence of other stressors have been evaluated in laboratory studies and suggest that pesticides, such as imidacloprid, in combination with pathogens may impact colony health and immune function in honey bees. It is believed that several neonicotinoid insecticides are implicated in the decline of honey bee populations, including the following: imidacloprid. clothianidin, thiamethoxam, and dinotefuran.

To provide necessary and sufficient written disclosure and enablement of the various embodiments of the present invention, the following references are incorporated by reference in their entireties: 20110269119 to Hutchinson, et al.; 20130064796 to Hamdi; 20140212520 to Del Vecchio, et al.; U.S. Pat. No. 9,017,718 to Tan; 20140065218 to Lang et al.; U.S. Pat. Nos. 6,599,883; 8,383,201; 5,158,789; 20070218114 to Sorousch; 20040136923 to Davidson; U.S. Pat. No. 8,999,372 to Davidson; 20090196907 to Bunick; 20090196908 to Lee; 20030124178 to Haley; 20070293587 to Haley; 20100285098 to Haley; 2006-0204591 to Burrell; U.S. Pat. No. 7,087,249 to Burrelll; U.S. Pat. No. 6,210,699 to Acharya; U.S. Pat. No. 8,865,211 to Tzannis; 20140199266 to Park; U.S. Pat. No. 6,599,883 to Romeo; PCT/US2008/080362 to Dussia; 2007-0218114 to Duggan; 2004-0136923 to Davidson; 20110142942 to Schobel; 20040120991 to Gardner et al.; Fuchs et al. U.S. Pat. No. 4,136,162; 20040136923 to Davidson; U.S. Pat. No. 4,163,777 to Mitra; U.S. Pat. No. 5,002,970 to Eby, III; 20040096569 to Barkalow et al.; 20060035008 to Virgallito et al.; 20030031737 to Rosenbloom; U.S. Pat. No. 6,919,373 to Lam et al.; 20050196358 to Georglades et al.; U.S. Pat. No. 3,832,460 to Kosti; 2002002057 to Battey et al.; 20040228804 to Jones, et al.; U.S. Pat. No. 6,054,143 to Jones; U.S. Pat. No. 5,719,196 to Uhari; 20150150792 to Klingman; 20140333003 to Allen; 20140271867 to Myers; 20140356460 to Lutin; 20150038594 to Borges; U.S. Pat. No. 6,139,861 to Friedman; 20150216917 to Jones; 20150361436 to Hitchcock; 20150353901 to Liu; U.S. Pat. No. 9,131,884 to Holmes; 20150064138 to Lu;

20150093473 to Barrangou; 20120027786 to Gupta; 20150166641 to Goodman; 20150352023 to Berg; 20150064138 to Lu; 20150329875 to Gregory; 20150329555 to Liras; 20140199281 to Henn; U.S. 20050100559 (proctor and Gamble); 20120142548 to Corsi et al.; U.S. Pat. No. 6,287,610, U.S. Pat. No. 6,569,474, U.S. 20020009520, U.S. 20030206995, U.S. 20070054008; and U.S. Pat. No. 8,349,313 to Smith; and U.S. Pat. No. 9,011,834 to McKenzie; 20080267933 to Ohlson et al.; 20120058094 to Blasser et al.; U.S. Pat. No. 8,716,327 to Zhao; 20110217368 to Prakash et al.; 20140044734 to Sverdlov et al.; 20140349405 to Sontheimer; 20140377278 to Elinav; 20140045744 to Gordon; 20130259834 to Klaenhammer; 20130157876 to Lynch; 20120276143 to O'Mahony; 20150064138 to Lu; 20090205083 to Gupta et al.; 20150132263 to Liu; and 20140068797 to Doudna; 20140255351 to Berstad et al.; 20150086581 to Li; PCT/US2014/036849; 20160348120 to Esvelt, et al. and WO 2013026000 to Bryan.

It is believed that honey bees are highly dependent on their hive-mates for acquisition of their normal gut bacteria. Each worker acquires a fully expanded, typical gut community before it leaves the hive. Different colonies may maintain distinct community profiles at the strain level and thus, biological variation among colonies results in part from variation in gut communities. Worker bees develop a characteristic core microbiota within hives. Some Gram-positive members of the core microbiota can be acquired through contact with hive surfaces. Gram-negative species, *S. alvi, G. apicola*, and *F. perrara*, appear to be acquired through contact with nurse bees or with fresh feces but not through oral trophallaxis. The eusocial honey bees and bumble bees harbor two specialized gut symbionts, *Snodgrassella alvi* and *Gilliamella apicola*, and these microorganisms are specific to bees, with different strains of these bacteria assorting to host species.

Workers initially lack gut bacteria and gain large characteristic communities in the ileum and rectum within 4 to 6 days within hives. The core species of Gram-negative bacteria, *Snodgrassella alvi, Gilliamella apicola*, and *Frischella perrara*, are believed to be conveyed via nurses or hindgut material, whereas some Gram-positive species are often transferred through exposure to hive components. *G. apicola* and *S. alvi* are mutualistic symbionts with roles in both pathogen defense and nutrition. Their highly restricted distribution and phylogenetic correlation with their hosts are suggestive of a lengthy coevolutionary history with bees and with each other.

Workers possess a consistent set of nine bacterial species that are observed in bees collected worldwide and that dominate their gut communities. Members of the core gut community include *Snodgrassella alvi* (Betaproteobacteria: Neisseriales) and *Gilliamella apicola* and *Frischella perrara* (Gammaproteobacteria: Orbales); three species of Alphaproteobacteria ("Alpha-1," "Alpha-2.1," and "Alpha-2.2" and three Gram-positive species ("Bifido," corresponding to *Bifidobacterium asteroides* and "Firm-4" and "Firm-5" [both Firmicutes: Lactobacillaceae]. Discrete communities are found in different gut compartments: the crop and midgut contain very few bacteria, whereas hindgut compartments (ileum and rectum) house large communities with characteristic compositional profiles.

Interestingly, queen gut microbiomes do not always reflect those of the workers who tend to them and often lack many of the bacteria that are considered to be "core" to workers. Worker gut microbiotas are relatively consistent across unrelated colony populations and the microbiotas of the related queens are highly variable. Queen bee microbiomes are dominated by enteric bacteria in early life but are comprised primarily of α-proteobacteria at maturity. Bacterial communities in mature queen guts were similar in size to those of mature workers and were characterized by dominant and specific α-proteobacterial strains known to be associated with worker hypopharyngeal glands. It is believed that queen guts are colonized by bacteria from workers' glands.

Workers emerge from the pupal stage without the core gut bacteria and are fully colonized within several days postemergence. Early culture-based studies noted that bees removed from frames as pupae could remain free of gut bacteria through adulthood. During the pupal stage, the shedding of the integument and gut intima bars the carriage of gut microbes from the larval stage to the adult stage. Newly emerged *A. mellifera* workers (NEWs) are fed via oral trophallaxis by attendant nurse workers, consume bee bread, the fermented pollen food source stored within hives, and have many encounters with adult bees within the hive. Interactions with older bees as well as contact with the comb and bee bread are all potential inoculation routes for young workers.

Honey bees (*Apis* spp.) and bumble bees (*Bombus* spp) possess a distinctive gut microbiota dominated by three groups, *S. alvi, G. apicola*, and *Lactobacillus* spp., and these form the majority of the gut community. From an evolutionary perspective, specialized gut bacteria represent a unique but ubiquitous form of symbiosis that has thus far escaped close scientific scrutiny. For the eusocial corbiculate bees, there appear to be at least 4 lineages of gut bacteria exhibiting host specificity: *S. alvi, G. apicola, Lactobacillus* spp, and *Bifidobacterium* spp. *Gilliamella apicola* and *Snodgrassella alvi* are dominant members of the honey bee (*Apis* spp.) and bumble bee (*Bombus* spp.) gut microbiota.

Both *G. apicola* and *S. alvi* have relatively small genomes with reduced functional capabilities, which is consistent with their being specialized gut symbionts. *S. alvi* has lost the ability to use carbohydrates for carbon or energy: The glycolysis (Embden-Meyerhof-Parnas), pentose phosphate, and Entner-Doudoroff pathways needed to convert sugars to pyruvate are all missing key enzymes, and thus are predicted to be nonfunctional. This is surprising, considering that the bee diet consists mainly of carbohydrates. Instead, *S. alvi* possesses transporters for uptake of carboxylates, such as citrate, malate, α-ketoglutarate, and lactate. These can be used directly in the tricarboxylic acid cycle (TCA) cycle or, in the case of lactate, can be converted to pyruvate via lactate dehydrogenase. *S. alvi* is an obligate aerobe possessing NADH dehydrogenase and cytochrome bo and bd oxidases, but it lacks the TCA cycle enzyme succinyl-CoA synthetase, which catalyzes the interconversion of succinyl-CoA and succinate.

In particular embodiments, the present invention is directed to a system and method used for the biological control of the welfare of bees, and for prophylaxis and treatment of pathological disorders of bees caused by insecticides, and especially neonicotinoids. In certain embodiments, bacteria are modified, preferably via the CRISPR-Cas system, and such bacteria are then provided to honey bees in a fashion such that they can reside in the gut of the honey bee, such bacteria selected from the group consisting of: *S. alvi, G. apicola, Lactobacillus* spp, and *Bifidobacterium* spp. *Gilliamella apicola* and *Snodgrassella alvi*. The CRISPR-Cas system is employed to enable such modified species to degrade neonicotinoids. CRISPR elements, another widespread system of phage defense, are abundant in *G. apicola* genomes and may act synergistically with restriction modification systems.

In other embodiments, still other bacteria are introduced into a bee hive environment in a manner such that the bacteria are incorporated into the gut microbiota of at least worker bees or nurse bees, such that the colony can then acquire the ability to assimilate or degrade neonicotinoids that they are exposed to. In this regard, the following bacteria may be employed: *Lactobacillus paracasei* ssp., *Bifidobacterium bifidum, Lactobacillus acidophilus, Lactococcus lactis, Bifidobacterium animalis, Lactobacillus thermophilus,* and *Bacillus clausii; Lactobacillus plantarum* YML001, *Lactobacillus plantarum* YML004 and *Leuconostoc citreum* KM20; *ochrobactrum intermedium* SCUEC4 strain, wherein the preservation number is CCTCC NO:M2014403; *ochrobactrum intermedium* strain LMG3306. Particularly preferred microbes to employ, whether for extraction of their neonicotinoid genes for transplantation into the gut microbes of honey bees, or for the microbes inclusion as a microbe in the gut of honey bees, is a member of the genus *ochrobactrum*, in the alpha-2 subgroup of the domain Proteobacteria.

Other embodiments of the present invention are directed to modification of the bat gut microbiome so as to enhance the health and survival of bats, e.g. by providing bats with bacteria that can degrade neonicotinoids. In doing so, the adverse effects of WNS can be ameliorated. There are over 190 species within the Phyllostomidae, the New World leaf-nosed bat family. These bats are found from southern USA and northern Mexico to Argentina and are the most ecologically diverse family within the order Chiroptera. They show an evolutionary diversification of dietary strategies from insectivory to diets that include blood, meat from small vertebrates, nectar, fruit and complex omnivorous mixtures. Microbiomes of these bat species include: Gamma-, Alpha-, and Delta-proteobacteria, Tenericutes, Firmicutes, Bacteroidetes, Planctomycetes, Cyanobacteria; Proteobacteria; Gammaproteobacteria; Enterobacteriales; Pasteurella; Deltaproteobacteria; Desulfurellales, Syntrophobacterales, Myxococcales; Rhodospirillales, Rhodobacterales, Rhizobiales, Rickettsiales; Firmicutes; Clostridia; Bacilli; and Cyanobacteria. One striking difference in microbiome composition between plant—(fruit and nectar) vs. animal-eating bats (insectivores and sanguivores) is the great abundance of Crenarchaeota in the later. Overall, archaea are more abundant in the insect and blood eating bats.

The beneficial bacteria on the skin of bats provide vital functions, including processing of skin proteins, freeing fatty acids to reduce invasion of transient microorganisms, and inhibition of pathogenic microorganisms. While some probiotics have been contemplated in the biological control of disease in both aquaculture and agriculture, they have yet to be widely implemented in controlling wildlife disease.

In preferred embodiments of the present invention, bacteria that naturally occur in the bat microbiota are used and even more preferably, certain strains that have been modified to enhance their effectiveness and survival on a bat's skin or gut environment, and/or modified to have particular antibiotic characteristics, are employed. Those that are able to colonize the bat's skin and/or gut are preferred. Augmentation prior to *P. destructans* exposure is preferably used, but in other embodiments, bacterial augmentation even after exposure to *P. destructans* can be used to displace such pathogen.

One objective is to employ a strain of bacteria that can effectively persist on bat skin at high enough concentrations to limit *P. destructans* growth below levels that cause lethal disease.

In certain embodiments, the group of bacteria used comprise *Pseudomonas fluorescens*, which is known to produce a suite of antifungal compounds that can inhibit many plant fungal pathogens as well as the amphibian fungal pathogens, *Batrachochytrium dendrobatidis*. Some strains in the *P. fluorescens* group are also capable of producing mycolysing enzymes that can colonize the mycelia and conidia of fungi rendering them no longer viable. Thus, this bacteria, whether wild type or modified as described herein, is employed in various methods and systems as set forth herein as a biological control agent for reducing infection intensity and increasing survival of bats exposed to *P. destructans*.

Isolation of such antifungal bacteria can be obtained from the skin of bat species that appear to be better at surviving WNS, and thus, isolates from the skin of *E. fuscus*, which has lower mortality from WNS compared to other species, is preferably employed. In other embodiments, strains of *P. fluorescens* (PF3 and PF4) are used.

Administration of effective bacteria that can beneficially assist bats in combating the ill effects of neonicotinoids can be achieved in many ways, including but not limited to spraying colonies of bats with bacterial solutions; providing such bacterial solutions in places where bats frequent in a manner that they will be exposed to the same; purposeful capture and inoculation of members of a colony such that they will be able to then spread the bacteria to other bats in a colony, effectively inoculating the entire colony.

Certain aspects of the present invention are directed to employing genes from the microbe *ochrobactrum intermedium* such that bats are able to assimilate and degrade neonicotinoids. Other embodiments employ inoculation of bats with a culture of neonicotinoid degrading bacteria, such as one or more of *ochrobactrum intermedium, Agrobacterium tumefaciens* S33, *Apergillus oryzae, Pseudomonas putida* S16; *Arthrobacter nicotinovarans, microsporum gypseum, pellicularia filamentosa* JTS-208, *pseudomonas* sp. 41; *Microsporum gypseum; Pseudomonas* ZUTSKD; *aspergillus oryzae* 112822; and *ochrobactrum intermedium* DN2. Preferably wherein the bacteria collection or culture comprises *ochrobactrum intermedium*, collection number CGMCC NO. 8839 is used. The invention further provides applications of the *ochrobactrum intermedium* to foster degradation of neonicotinoid insecticides by bats while the microbe exists in the gut or skin of the bats, the gut of honey bees and in butterflies.

CRISPR systems may be employed to insert desired genes into the above mentioned (as well as others) microbes that inhabit the bat gut or skin so as to degrade particular insecticides, including neonicotinoids. The bat microbiome enhances host functions, contributing to host health and fitness. One aspect of the present invention is directed to improving bat fitness by modifying the bat microbiome, thus engineering evolved microbiomes with specific effects on the host bat fitness. Thus, by employing host-mediated microbiome selection, one is able to select and modify microbial communities indirectly through the host, thus influencing the bat microbiome and positively affecting bat fitness. The methods that may be used to impose artificial selection on the bat microbiome include various techniques known to those of skill in the art, including CRISPR-Cas and Cpl1 systems. Thus, while particular cultures of particular microbes can be purposefully included into bat populations so as to inhabit their gut or skin microbiome, and by doing so, providing the bats with the ability to degrade neonicotinoids, other embodiments are directed to engineering a modification of the bat gut or skin microbes that do not already possess such neonicotinoid degradation genes.

In certain embodiments, xenobiotic detoxification is employed. In particular embodiments, the conversion of lipid-soluble substances to water-soluble, excretable metabolites is achieved. In a primary detoxification step, a toxin structure is enzymatically altered and rendered unable to interact with lipophilic target sites. Such functionalization is effected primarily by cytochrome P450 monooxygenases (P450) and carboxylesterases (CCE), although other enzymes, including flavin-dependent monooxygenases and cyclooxygenases may also be employed. Further reactions typically involve conjugation of products of the above referenced step to achieve detoxification for solubilization and transport. Glutathione-S-transferases (GST) are the principal enzymes used, although other enzymes may include glycosyltransferases, phosphotransferases, sulfotransferases, aminotransferases, and glycosidases. Nucleophilic compounds can be rendered hydrophilic by UDP-glycosyltransferases. The final stage of detoxification involves transport of conjugates out of cells for excretion. Among the proteins involved in this process are multidrug resistance proteins and other ATP-binding cassette transporters.

In particular embodiments, the present invention is directed to a system and method used for the biological control of the welfare of bats, and for prophylaxis and treatment of pathological disorders of bats caused by insecticides, and especially neonicotinoids. In certain embodiments, bacteria are modified, preferably via the CRISPR-Cas system, and such bacteria are then provided to bats in a fashion such that they can reside in the gut or skin of the bats, such bacteria selected from the group consisting of: Gamma-, Alpha-, and Delta-proteobacteria, Tenericutes, Firmicutes, Bacteroidetes, Planctomycetes, Cyanobacteria; Proteobacteria; Gammaproteobacteria; Enterobacteriales; Pasteurella; Deltaproteobacteria; Desulfurellales, Syntrophobacterales, Myxococcales; Rhodospirillales, Rhodobacterales, Rhizobiales, Rickettsiales; Firmicutes; Clostridia; Bacilli; and Cyanobacteria.

In other embodiments, still other bacteria are introduced into a bat colony environment in a manner such that the bacteria are incorporated into the gut and/or skin microbiota of at least some bats, which can then "infect" other bats with such bacteria, and in so doing, the colony of bats can then acquire the ability to assimilate or degrade neonicotinoids that it is exposed to. In this regard, the following bacteria may be employed: *Lactobacillus paracasei* ssp., *Bifidobacterium bifidum, Lactobacillus acidophilus, Lactococcus lactis, Bifidobacterium animalis, Lactobacillus thermophilus*, and *Bacillus clausii; Lactobacillus plantarum* YML001, *Lactobacillus plantarum* YML004 and *Leuconostoc citreum* KM20*; ochrobactrum intermedium* SCUEC4 strain, wherein the preservation number is CCTCC NO:M2014403; *ochrobactrum intermedium* strain LMG3306. Particularly preferred microbes to employ, whether for extraction of their neonicotinoid genes for transplantation into the gut and/or skin microbes of bats, or for the microbes inclusion as a microbe in the gut or skin of bats, is a member of the genus *ochrobactrum*, in the alpha-2 subgroup of the domain Proteobacteria.

While not bound by theory, it is believed that still other microbes may be employed in various embodiments of the present invention to address the objective of degrading neonicotinoid-like compounds, such bacteria showing an ability to degrade nicotine. The CRISPR-Cas system is employed to enable such modified species to degrade neonicotinoids. Thus, such system can be used to provide gut or skin bacteria that may grow on the bat skin or gut and can include genes that achieve desired degradation of neonicotinoids via the use of or presence of such genes in nicotine degrading organisms, such as *Agrobacterium tumefaciens* S33, *Apergillus oryzae, Pseudomonas putida* S16; *Arthrobacter nicotinovarans, microsporum gypseum, pellicularia filamentosa* JTS-208, *pseudomonas* sp. 41; *Microsporum gypseum; Pseudomonas* ZUTSKD; *aspergillus oryzae* 112822; and *ochrobactrum intermedium* DN2.

Microbial symbionts are important for host organisms, and insects rely on the communities of microorganisms in their guts for several functions. Hosts have evolved a range of mechanisms to protect themselves against parasites that are a large threat to their fitness. These defenses can extend beyond intrinsic host immunity and incorporate aspects of the environment in which host and parasite interact. Monarch butterfly (*Danaus plexippus*) larvae actively consume milkweeds (*Asclepias* spp.) that contain secondary chemical compounds, named cardenolides, which reduce parasite infection and virulence.

*Commensalibacter* is a genus of acetic acid bacteria and 16S rRNA gene sequences related to the *Commensalibacter* genus have been recovered from the guts of *Drosophila* species, honey bees, and bumble bees, as well as from *Heliconius erato* butterflies. The type strain *Commensalibacter intestini* A911 was isolated from *Drosophila* intestines, and the genome sequence of a *Commensalibacter* symbiont isolated from a monarch butterfly has been reported. *Commensalibacter papalotli* strain MX01, was isolated from the intestines of an overwintering monarch butterfly. The 2,332,652-bp AT-biased genome of *C. papalotli* MX01 is the smallest genome for a member of the *Acetobacteraceae.*

In certain embodiments, *Commensalibacter* bacteria are modified to render them able to degrade neonicotinoid insecticides and such bacteria are then purposefully provided to the gut biome of monarch butterflies to enable the butterflies to degrade such pesticides, and thus survive and remain viable for reproduction. In a particular embodiment, the genes responsible for the ability to degrade neonicotinoids are derived from the *ochrobactrum intermedium* SCUEC4 strain, wherein the preservation number is CCTCC NO:M2014403; and/or *ochrobactrum intermedium* strain LMG3306.

CRISPR systems may be employed to insert desired genes into various bacteria that can survive in the gut of the monarch butterfly such that these microbes can degrade particular insecticides, including neonicotinoids.

One aspect of the present invention is directed to improving monarch butterfly fitness by modifying the monarch butterfly microbiome, either by incorporation of select species of bacteria into existing gut microbiomes of the monarch butterfly, or by incorporation of genetic elements into existing bacteria within a monarch butterfly's gut such that the modified microbe is able to degrade neonicotinoids. These engineered microbiomes are purposefully designed to have with specific beneficial effects on the host monarch butterfly fitness. Thus, by employing host-mediated microbiome selection, one is able to select and modify microbial communities indirectly through the host, thus influencing the monarch butterfly microbiome and positively affecting monarch butterfly fitness. The methods that may be used to impose artificial selection on the monarch butterfly microbiome include various techniques known to those of skill in the art, including CRISPR-Cas and Cpl1 systems. Thus, particular cultures of particular microbes can be purposefully included into monarch butterfly populations so as to inhabit their gut microbiome, and by doing so, provide the monarch butterflies with the ability to degrade neonicotinoids. Other embodiments are directed to engineering a modification of the monarch butterfly gut microbes that do not already possess such neonicotinoid degradation genes.

Detoxification gene inventory reduction may reflect an evolutionary history of consuming relatively chemically benign nectar and pollen. Thus, certain embodiments are directed to the development of predictable microbiome-based biocontrol strategies by providing the ability of monarch butterflies to degrade or otherwise assimilate insecticides or other chemical agents, including neonicotinoids. Such a novel biocontrol strategy can not only be used to suppress pathogens, but can also be effectively used to establish microbiomes in a desirable beneficial composition for particular purposes.

In certain embodiments, xenobiotic detoxification is employed to address the problems associated with monarch butterfly health. In particular embodiments, the conversion of lipid-soluble substances to water-soluble, excretable metabolites is achieved. In a primary detoxification step, a toxin structure is enzymatically altered and rendered unable to interact with lipophilic target sites. Such functionalization is effected primarily by cytochrome P450 monooxygenases (P450) and carboxylesterases (CCE), although other enzymes, including flavin-dependent monooxygenases and cyclooxygenases may also be employed. Further reactions typically involve conjugation of products of the above referenced step to achieve detoxification for solubilization and transport. Glutathione-S-transferases (GST) are the principal enzymes used, although other enzymes in insects may include glycosyltransferases, phosphotransferases, sulfotransferases, am inotransferases, and glycosidases. Nucleophilic compounds can be rendered hydrophilic by UDP-glycosyltransferases. The final stage of detoxification involves transport of conjugates out of cells for excretion. Among the proteins involved in this process are multidrug resistance proteins and other ATP-binding cassette transporters.

Any one or more of appropriate bacteria can be modified to express particular genes that have been shown (for example by its inclusion in the bacteria *ochrobactrum intermedium*) to degrade neonicotinoids in a manner that preserves monarch butterfly health. One of skill in the art can address compatibility issues with respect to the use of such bacteria and can make modifications thereto to render it tolerable and viable in the gut microbiome of the monarch butterfly. Genetic modification of existing microbes in the monarch butterfly gut can also be performed to render such native bacteria able to produce agents effective in degrading neonicotinoids.

Impacts to monarch butterflies from sublethal exposure to neonicotinoids, such as imidacloprid, especially in the presence of other stressors, is believed to result in severe and significant dysfunctions within and have an adverse impact on monarch colony health and to the immune function in individual monarch butterflies. It is believed that several neonicotinoid insecticides are implicated in the decline of monarch butterfly populations, including the following: imidacloprid, clothianidin, thiamethoxam, and dinotefuran.

In particular embodiments, the present invention is directed to a system and method used for the biological control of the welfare of monarch butterflies, and for prophylaxis and treatment of pathological disorders of monarch butterflies caused by insecticides, and especially neonicotinoids. In certain embodiments, bacteria are modified, preferably via the CRISPR-Cas system, and such bacteria are then provided to monarch butterflies in a fashion such that they can reside in the gut of the monarch butterfly, such bacteria selected from the group consisting of one or more bacteria in six bacterial families: the Acetobacteraceae (Alphaproteobacteria), Moraxellaceae and Enterobacteriaceae (Gammaproteobacteria), Enterococcaceae and Streptococcaceae (Firmicutes), and an unclassified family in the Bacteroidetes phylum. In particular embodiments, the bacteria employed in the present invention include one or more of the following: *Commensalibacter*, and in particular *Commensalibacter intestini* A911 and *Commensalibacter papalotli* strain MX01; *Lactobacillus paracasei* ssp., *Bifidobacterium bifidum, Lactobacillus acidophilus, Lactococcus lactis, Bifidobacterium animalis, Lactobacillus thermophilus*, and *Bacillus clausii; Lactobacillus plantarum* YML001, *Lactobacillus plantarum* YML004 and *Leuconostoc citreum* KM20; *ochrobactrum intermedium* SCUEC4 strain, wherein the preservation number is CCTCC NO:M2014403; *ochrobactrum intermedium* strain LMG3306. Particularly preferred microbes to employ, whether for extraction of their neonicotinoid genes for transplantation into the gut microbes of monarch butterflies, or for the microbes inclusion as a microbe in the gut of monarch butterflies, is a member of the genus *ochrobactrum*, in the alpha-2 subgroup of the domain Proteobacteria.

Modifying the gut microbiota of monarch butterflies to provide them with the ability to consume chemically defended plants can thus be achieved by varying the monarch butterflies associated microbial communities. Different microbes may be differentially able to detoxify compounds toxic to the monarch or may be differentially resistant to the potential antimicrobial effects of some compounds.

In certain embodiments, the administration of effective bacteria that can beneficially assist monarch butterflies in combating the ill effects of neonicotinoids can be achieved in many ways, including but not limited to spraying colonies of butterflies or caterpillars that will emerge as butterflies with bacterial solutions; providing such bacterial solutions in places where monarch butterflies frequent in a manner that they will be exposed to the same, such as by having bacteria provide in sweetened solutions that monarch butterflies are drawn to; purposeful capture and inoculation of members of a colony such that they will be able to then spread the bacteria to other bats in a colony, effectively inoculating an entire colony of monarch butterflies.

As one of skill in the art of living will appreciate, the reason to preserve nature is not merely within the realm of science, as beauty and literature are rooted in those creatures who share this earth with us. The philosophers of the past recognized this fact. Nietzsche once said: “And to me also, who appreciate life, the butterflies, and soap-bubbles, and whatever is like them amongst us, seem most to enjoy happiness.” Our treasure lies in the beehive of our knowledge. We are perpetually on the way thither, being by nature winged insects and honey gatherers of the mind.” Aristotle chimed in: “As the eyes of bats are to the blaze of day, so is the reason in our soul to the things which are by nature most evident of all.” Karl von Frisch said “Nature has unlimited time in which to travel along tortuous paths to an unknown destination. The mind of man is too feeble to discern whence or whither the path runs and has to be content if it can discern only portions of the track, however small.” So as Nabokov suggested, “do what only a true artist can do . . .

pounce upon the forgotten butterfly of revelation." "Literature and butterflies are the two sweetest passions known to man."

While specific embodiments and applications of the present invention have been described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention. Those skilled in the art will appreciate that the conception, upon which this disclosure is based, may readily be utilized as a basis for designing of other methods and systems for carrying out the several purposes of the present invention to instruct and encourage the prevention and treatment of various human diseases. It is important, therefore, that the claims be regarded as including any such equivalent construction insofar as they do not depart from the spirit and scope of the present invention.

What is claimed is:

1. A method for providing a honey bee with the ability to assimilate neonicotinoid pesticides, comprising, inoculating a honey bee with a culture of neonicotinoid degrading bacteria, wherein the neonicotinoid degrading bacteria is *Ochrobactrum intermedium.*

2. The method as set forth in claim 1, wherein the neonicotinoid is selected from the group consisting of acetamiprid, clothianidin, dinotefuran, nitenpyram, thiacloprid, and thiamethoxam.

3. The method as set forth in claim 1, wherein the neonicotinoid is acetamiprid.

4. The method as set forth in claim 1, wherein the neonicotinoid is clothianidin.

5. The method as set forth in claim 1, wherein the neonicotinoid is dinotefuran.

6. The method as set forth in claim 1, wherein the neonicotinoid is nitenpyram.

7. The method as set forth in claim 1, wherein the neonicotinoid is thiacloprid.

8. The method as set forth in claim 1, wherein the neonicotinoid is thiamethoxam.

* * * * *